United States Patent [19]

Schwartz

[11] 4,003,903

[45] Jan. 18, 1977

[54] N-ACYL-N-NORSALUTARIDINES AND PROCESS FOR MAKING THEM

[75] Inventor: Martin Alan Schwartz, Tallahassee, Fla.

[73] Assignee: Florida Board of Regents, Tallahassee, Fla.

[22] Filed: Feb. 12, 1975

[21] Appl. No.: 549,491

[52] U.S. Cl. .............................................. 260/285
[51] Int. Cl.$^2$ ...................................... C07D 217/06
[58] Field of Search ........................ 260/285, 289 A

[56] References Cited

OTHER PUBLICATIONS

Schwartz et al., J. Am. Chem. Soc. 95, 612–613 (1973).

*Primary Examiner*—G. Thomas Todd

[57] ABSTRACT

N-acyl-N-norsalutaridines can be made by oxidative coupling of N-acyl-N-norreticulines using thallium tristrifluoroacetate or a coordinating agent and an oxidizing agent. The N-acyl-N-norsalutaridines can be converted to thebaine, N-northebaine, and N-substituted-N-northebaines, which can be converted to opium alkaloids and related compounds.

19 Claims, No Drawings

N-ACYL-N-NORSALUTARIDINES AND PROCESS FOR MAKING THEM

The invention described herein was made in the course of work under a grant or award from the Department of Health, Education, and Welfare.

BACKGROUND OF THE INVENTION

Thebaine is used commercially as starting material for the narcotic analgesics oxycodone and oxymorphone, the narcotic antagonist naloxone and the narcotic antitussive dihydrocodeinone. It can also be used as starting material for the narcotic analgesics codeinone, codeine and morphine, the narcotic antagonist naltrexone, and other medicinally useful narcotic and non-narcotic substances.

Thebaine, codeine and morphine are produced by the opium poppy (*Papaver somniferum*). For commercial use, these compounds are obtained solely by extraction from opium or from opium poppy stems and capsules. They have been produced on laboratory scale by totally synthetic routes, but these syntheses involved many steps and very low overall yields, and were therefore not suitable for commercial production.

The biosynthetic pathway by which the opium poppy produces these compounds has been established and is presented below:

Equivalent structures for Reticulene (The numbering system for thebaine is used here and below for salutaridine and salutaridinol to aid in showing the equivalence.)

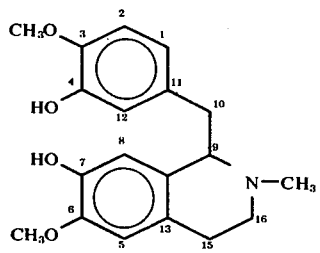

Usual Representation
Biosynthetic Pathway

=

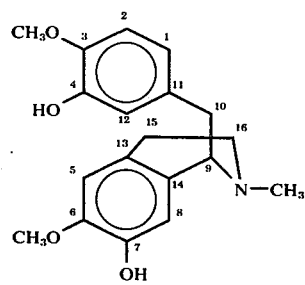

Equivalent Structure

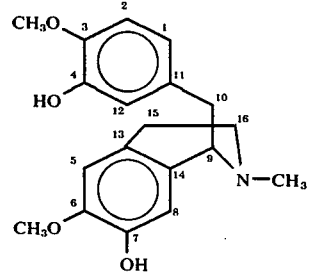

1
Reticuline

→

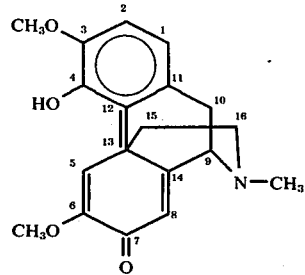

2
Salutaridine

2 →

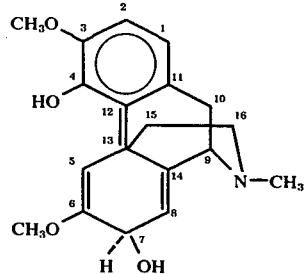

3
Salutaridinol

3 →

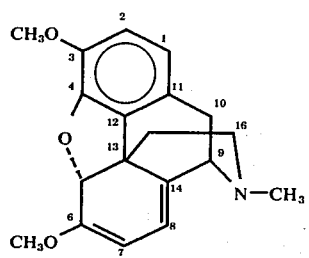

4
Thebaine

→

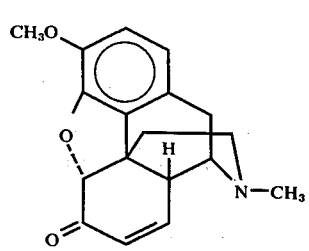

5
Codeinone

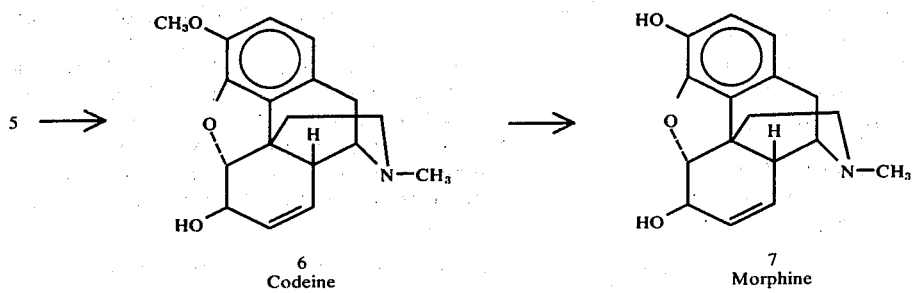

6
Codeine

7
Morphine

Many attempts have been made to convert reticuline (1) to salutaridine (2) in the laboratory. With one exception, these attempts have produced only isosalutaridine (8) and/or isoboldine (9).

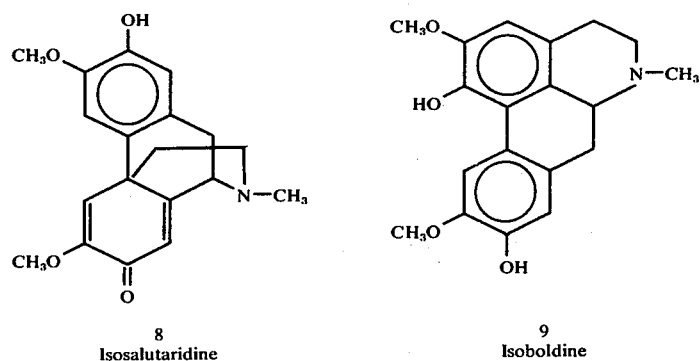

8
Isosalutaridine

9
Isoboldine

The exception was Barton and coworkers' detection, via isotope dilution techniques, of a 0.03% yield of salutaridine (2) from ferricyanide oxidation of reticuline (1). [Barton et al., *J. Chem. Soc.,C*, 128 (1967)]. Salutaridine has also been produced from reticuline by enzymic conversion. (Schoenewaldt et al., U.S. Pat. No. 3,785,927, issued Jan. 15, 1974.)

Attempts have also been made to convert N-ethoxycarbonyl-N-norreticuline to N-ethoxycarbonyl-N-norsalutaridine, but these produced only the corresponding N-norisoboldine (Kametani et al., *Tetrahedron*, 25, 3667 (1969)) or N-norisosalutardine (Bobbitt, *Heterocycles*, 1, 181 (1973)) or no recoverable product (Cava et al., *Tetrahedron*, 25, 2795 (1969)).

SUMMARY OF THE INVENTION

This invention is a method for making N-acyl-N-norsalutaridines which comprises reacting an N-acyl-N-norreticuline with thallium tristrifluoroacetate (TTFA), which is both a coordinating agent and an oxidizing agent. Separate coordinating and oxidizing agents can be used in place of the TTFA. The reaction can be represented as follows:

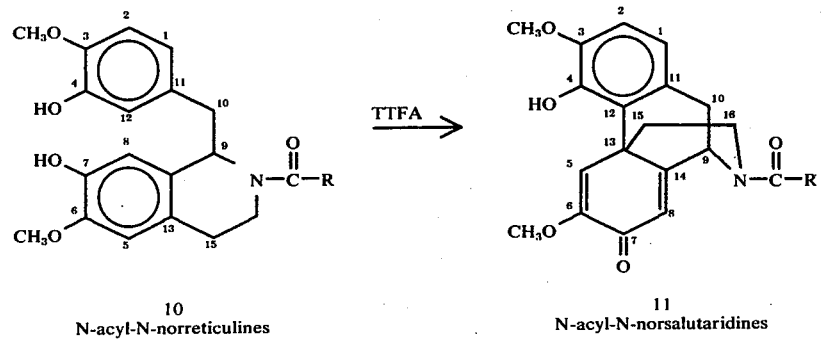

10
N-acyl-N-norreticulines

11
N-acyl-N-norsalutaridines wherein R is hydrogen or an organic radical such as $C_1$–$C_{12}$ alkyl, $C_6$–$C_{12}$ aryl, $C_3$–$C_7$ cycloalkyl, $C_1$–$C_{12}$ alkoxy, $C_6$–$C_{12}$ aryloxy, $C_5$–$C_6$ cycloalkoxy, and $C_3$–$C_{12}$ alkenyloxy. The above radicals can be substituted with 1–7 halogens selected from fluorine and chlorine. The $C_1$–$C_6$ alkyl and $C_1$–$C_6$ alkoxy radicals can be substituted with $C_1$–$C_6$ alkoxy or $C_6$–$C_{12}$ aryl. The aryl and aryloxy radicals and the aryl portions of the aryl-substituted alkyl and alkoxy radicals can be substituted with 1–2 $C_1$–$C_2$ alkoxy radicals.

Preferred R groups are $C_1$–$C_3$ alkoxy, benzyloxy, methylbenzyloxy, trifluoromethyl, difluoromethyl, trichloromethyl, methyl, hydrogen and cyclopropyl.

The N-acyl-N-norsalutaridines are novel compounds and are part of this invention. They are useful as intermediates for preparing thebaine, N-northebaine, and various N-substituted-N-northebaines, which are in turn useful as intermediates in the manufacture of opium alkaloids and related compounds.

DETAILS OF THE INVENTION

The reaction of this invention is carried out under anhydrous conditions in a non-polar aprotic solvent such as dichloromethane, chloroform, benzene, trichloroethylene, tetrachloroethylene, or carbon tetrachloride. A nitrogen, argon, or other inert atmosphere can be used, but is not considered necessary. Initial concentration of N-acyl-N-norreticuline (10) can be about 0.0001 to about 0.1 molar, preferably about 0.001 molar.

It is believed that the reaction involves an initial coordination of the metal with the reticuline followed by oxidation:

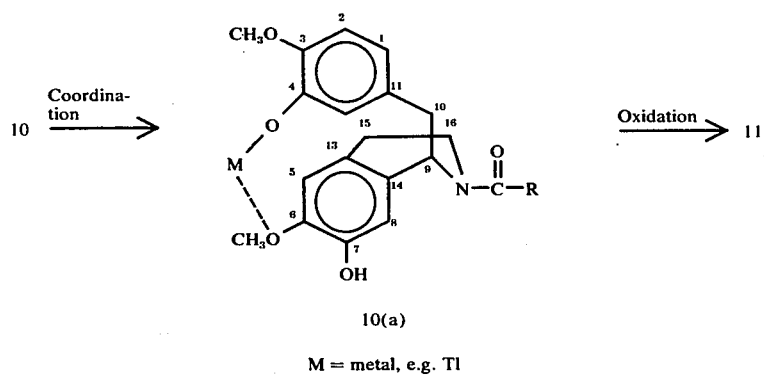

M = metal, e.g. Tl

The combined coordinating oxidizing agent TTFA is the preferred reagent, but separate coordinating and oxidizing agents can be used. Suitable coordinating agents include the trifluoroacetates, perchlorates, chlorides, bromides and iodides of palladium, copper, nickel, magnesium, calcium and lithium. Suitable oxidizing agents include manganese dioxide, silver carbonate, silver oxide, vanadyl chloride, ferric chloride and lead dioxide.

TTFA can be prepared as described in McKillop et al., Tetrahedron, 26, 4031 (1970). The amount of TTFA, $Ag_2CO_3$ or $Ag_2O$, when used, should be about 0.5–1.5, preferably 1, molar equivalent per mole of N-acyl-N-norreticuline.

The amount of $MnO_2$, $VOCl_3$, or $FeCl_3$ when used, should be about 1.5–2.5, preferably 2, molar equivalents per mole of N-acyl-N-norreticuline.

Initial reaction temperature can be between about −95° C. and +25° C. When TTFA is used, or when separate coordinating and oxidizing agents are used simultaneously, it is preferred to maintain the temperature below the temperature at which oxidation occurs for a period of time in order to maximize formation of the coordination complex (10a). Otherwise, N-acyl-N-norsalutaridine yield loss occurs because of direct oxidation of the reticuline analog (10) to the corresponding isoboldine.

The temperature at which oxidation begins varies with the various oxidizing agents. For example, for TTFA this temperature is about −30° C. but for $VOCl_3$, it is about −78° C. Thus, for example, with TTFA it is preferred to hold the reactants between about −95° and −30° C. for an initial period of about ½ to 3 hours, then raise the temperature to between about −30° and +25° C. for about ½ to 10 hours.

When separate coordinating and oxidizing agents are used, and the oxidizing agent is added after the coordination is complete, the same temperature can be used during both the coordination and oxidation stages.

Preparation of the N-acyl-N-norreticulines

The N-acyl-N-norreticulines (10) are prepared by conventional acylation of N-norreticuline. Racemic N-norreticuline can be prepared as described in Battersby et al., J. Chem. Soc., 3600 (1964). The racemate can be resolved as taught in Battersby et al., J. Chem. Soc. (C), 1052 (1966). The racemate or either enantiomer can be used in making the N-acyl-N-norreticulines, but it is preferred to use R-N-norreticuline, since this leads to the 9R-N-acyl-N-norsalutaridines thence to the 9R-thebaine and 9R-N-northebaines by the processes described below, and these are the enantiomers used commerically.

Preparation of N-ethoxycarbonyl-N-norreticuline is described in Kametani et al., Tetrahedron, 25, 3667 (1969). The N-acyl-N-norreticulines (10) wherein R is alkoxy, alkenyloxy, aryloxy, aralkoxy or cycloalkoxy are prepared similarly by substituting the appropriate chloroformate for ethyl chloroformate.

Preparation of N-trifluoroacetyl-N-norreticuline is described in Example 1 below. The N-acyl-N-norreticulines (10) wherein R is alkyl, aryl or cycloalkyl can be prepared similarly by substituting an appropriate anhydride or acid chloride for the trifluoroacetic anhydride. The N-formyl-N-norreticuline (R=H) can be made by substituting mixed formic/acetic anhydride for the trifluoroacetic anhydride.

Production of N-northebaine

N-acyl-N-norsalutaridines (11) wherein R is α-halosubstituted alkyl such as $CF_3$—, $CHF_2$, $CCl_3$—, $CH_3CCl_2$—, $CH_3CHF$— or $CF_3CF_2$—, can be converted to N-norsalutaridine (12)

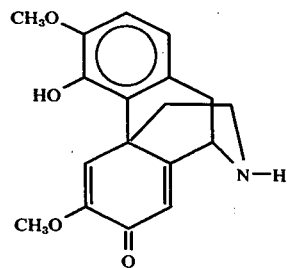

-continued

(12) N-norsalutaridine by hydrolysis with a weak base such as sodium or potassium carbonate or bicarbonate or ammonia in aqueous $C_1$–$C_4$ alkanol at room temperature to reflux temperature.

N-acyl-N-norsalutaridines (11) wherein R is alkoxy or aralkoxy, such as methoxy, ethoxy, propoxy or benzyloxy, can be converted to N-norsalutaridine (12) by hydrolysis with a strong base such as sodium or potassium hydroxide in aqueous $C_1$–$C_4$ alkanol at room temperature to 50° C.

N-acyl-N-norsalutaridines (11) wherein R is alkyl or aryl such as methyl or phenyl can be converted to N-norsalutaridine (12) by treatment with triethyloxonium fluoroborate (Meerwein's reagent) followed by hydrolysis in an aqueous alkanol solution of a weak base as described above or in dilute acetic acid at room temperature to reflux. Use of Meerwein's reagent to remove an N-benzoyl group is described in Muxfeldt et al., *J. Am. Chem. Soc.*, 87, 933 (1965); its use to remove an N-acetyl group is described in Haneffian, *Tetrahedron Letters*, 1549 (1967).

N-acyl-N-norsalutaridines (11) wherein R is aralkoxy such as benzyloxy can be converted to N-norsalutaridinol (13).

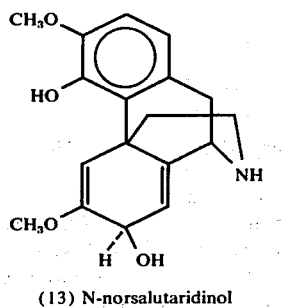

(13) N-norsalutaridinol by catalytic hydrogenation in presence of tristriphenylphosphine rhodium chloride, under conditions described in Boisonnas, Advances in Organic Chemistry, Vol. 3, p. 159 (1963).

N-acyl-N-norsalutaridines (11) wherein R is alkyl or aryl such as methyl or phenyl can be converted to N-norsalutaridinol (13) by diisobutyl aluminum hydride reduction followed by hydrolysis under mild conditions (water or weak base in aqueous alkanol, as described above). The reduction can be carried out in toluene at −78° C., the conditions described in Gutzwiller et al., *J. Am. Chem. Soc.*, 92, 204 (1970).

N-norsalutaridine (12) can be converted to N-norsalutaridinol (13) by hydride reduction, using $LiAlH_4$ in refluxing tetrahydrofuran or $NaBH_4$ in alcohol or Red-Al in refluxing benzene and N-norsalutaridinol (13) can be converted to N-northebaine (14)

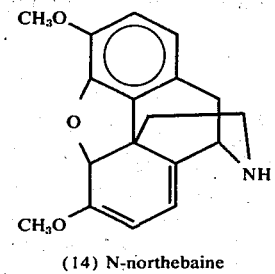

(14) N-northebaine by treatment with 1N HCl.

Production of Thebaine

N-acyl-N-norsalutaridines (11) wherein R is hydrogen, alkoxy, aryloxy, cycloalkyloxy or aralkoxy can be converted to salutaridinol (3) by hydride reduction using $LiAlH_4$ or $BH_3$ in refluxing tetrahydrofuran or Red-Al in refluxing benzene, and the salutaridinol (3) can be converted to thebaine (4) by treatment with 1N HCl. Barton et al., *J. Chem. Soc.* 2423 (1965).

Production of N-cycloalkylmethyl-N-northebaines

N-acyl-N-norsalutaridines (11) wherein R is cycloalkyl can be converted to N-cycloalkylmethyl-N-norsalutaridinols (15) by $LiAlH_4$ reduction under conditions described in Bartels-Keith, *J. Pharmacy and Pharmacology*, 16, p. 133 (1964), and the latter (15) can be converted to N-cycloalkylmethyl-N-northebaines (16) by treatment with 1N HCl.

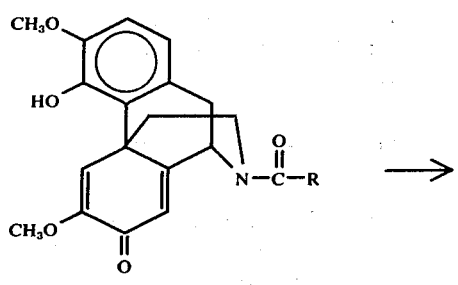

11
R is cycloalkyl

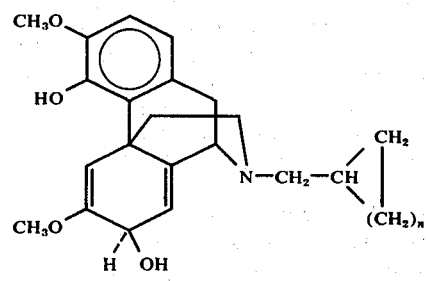

15
N-cycloalkylmethyl-N-norsalutaridinols
(n = 1–5)

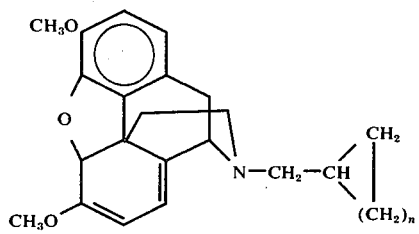

16 N-cycloalkylmethyl-N-northebaine

Uses of the Thebaines

The N-cycloalkylmethyl-N-northebaines 16 can be converted into N-cycloalkylmethyl-N-noroxymorphones by the known processes used to convert thebaine to oxymorphone.

The N-cycloalkylmethyl-N-noroxymorphones (e.g. naltrexone) are useful as narcotic antagonists, as described in U.S. Pat. 3,332,950; they can also be converted into N-cycloalkylmethyl-14-hydroxydihydronormorphine analgesics. e.g. nalbuphine, as described in U.S. Pat. No. 3,393,197.

Thebaine is used to make hydroxycodeinone (The Merck index, Eighth Edition, Merck & Co., Inc., Rahway N.J., U.S.A., 1968, p. 549). Hydroxycodeinone is used to make oxycodone (Id., p. 774). Oxycodone is used to make oxymorphone (U.S. Pat. No. 2,806,033). Oxymorphone can be converted to noroxymorphone which is used to make naloxone (U.S. Pat. No. 3,254,088), naltrexone (U.S. Pat. No. 3,332,950) and nalbuphine (U.S. Pat. No. 3,393,197).

N-northebaine can be converted to noroxymorphone by the same route used to convert thebaine to oxymorphone.

Thebaine can also be converted to codeinone (Conroy, J. Am. Chem. Soc., 77, 5960 (1955)), codeinone can be converted to codeine (Gates, J. Am. Chem. Soc., 75, 4340 (1953)), and codeine can be converted to morphine (Rapaport et al., J. Am. Chem. Soc., 73, 5900 (1951)). Thus, this invention permits total synthesis of these widely-used opium alkaloids.

EXAMPLE 1

(±)-N-Trifluoroacetyl-N-norsalutaridine

To a solution of 1.00 g (3.17 mmol) of (±)-N-norreticuline in 150 ml of dichloromethane was added 10 g (100 mmol) of anhydrous sodium carbonate and 16.8 g (11.2 ml, 80 mmol) of trifluoroacetic anhydride, and the mixture was stirred at room temperature (about 20° C.) for 2 hours. The solids were removed by filtration and the filtrate was evaporated under reduced pressure. To the residual oil was added 50 ml of water and enough methanol to cause solution, and the solution was stirred at about 50° C. for 3 hours. The mixture was diluted with another 40 ml of water and then was extracted thoroughly with chloroform. The organic layer was washed with water, dried over anhydrous sodium sulfate, and evaporated under reduced pressure.

The resulting oil was crystallized from chloroform-petroleum ether to give 1.0 g (2.43 mmol, 77%) of (±)-N-trifluoroacetyl-N-norreticuline, m.p. 128°–130° (m.p. 148°–152° from chloroform-methanol); IR (CHCl$_3$): 2.87, 5.97, 6.31, 6.68, 6.90, 7.00, 7.92, 8.06, 8.63, 8.79, 9.05, and 9.76 μ; NMR (CDCl$_3$) δ 6.83-6.30 (5 H,m) 5.56 (1H, t, J = 6.4), 3.88 (3H, s), 3.86 (3H, s), 3.58–2.61 (6H, m); mass spectrum (70 ev) m/e 411, 275, 274 (100%), 259, 220, 178, 162, 137.

Anal. Calc'd for C$_{20}$H$_{20}$NO$_5$F$_3$: C, 58.43; H, 4.90; N, 3.41; Found: C, 58.37; H, 5.10; N, 3.21. A solution of 103 mg (0.25mmol) of (±)-N-trifluoroacetyl-N-norreticuline in 50 ml of anhydrous, degassed dichloromethane was added dropwise to a slurry of 136 mg (0.25 mmol) of thallium tristrifluoroacetate in 250 ml of the same solvent, with stirring at −78° under nitrogen. The mixture was stirred at −78° for 3 hours, then was sealed under nitrogen and stirred at −20° for 10 hours, then at room temperature for 0.5 hour. The resulting deep green solution was evaporated under reduced pressure; the residue was dissolved in a minimum of chloroform and applied to a column of 25 g of silica gel, and was eluted with two 120 ml portions of chloroform.

The residue obtained upon evaporation of the eluate was subjected to preparative thin layer chromatography (developed in ether) to afford 15.6 mg. of oily product; crystallization from chloroform/hexane gave 11.0 mg. (11%) of the title compound; m.p. 196°–201° dec.; IR (CHCl$_3$): 2.85, 3.31, 5.92(sh), 5.96, 6.06, 6.16, 6.75, 6.97, 7.82, 8.12, 8.54, 8.74 and 9.14 μ, UV(EtOH): 239 and 282 nm (log ε 4.48 and 3.94); NMR (CDCl$_3$); 7.54 (1, s, H-5), 6.84 (1, d, 5 = 8.5, H-2), 6.68 (1, d, J = 8.5, H-1), 6.40 (1, dd, J = 5, 1.5, H-8), 3.93 (3.5, OCH$_3$—3), 3.77 (3, S, OCH$_3$—6), 3.34 (1, dd, J = 18, 5, H$_a$—10), and 3.15 (1, dd, J = 18, 1.5, H$_b$—10); mass spectrum (high resolution 70 ev) molecular ion at m/e 409.1150.

(Calculated for C$_{20}$H$_{18}$O$_5$NF$_3$ 409.1137). Anal. Calc'd. for C$_{20}$H$_{18}$O$_5$NF$_3$: C, 58.72; H, 4.44; N, 3.42; Found: C, 58.47, H, 4.50; N, 3.17

9R-N-trifluoroacetyl-N-norsalutaridine can be prepared by substituting R-N-norreticuline for (±)-N-norreticuline in this Example.

Example 2

(±)-N-Ethoxycarbonyl-N-norsalutaridine

The procedure of Example 1 was used, starting with 145 mg (0.375 mmol) of (±)-N-ethoxycarbonyl-N-norreticuline in place of (±)-N-trifluoroacetyl-N-norreticuline, to give 33.0 mg (23%) of the title compound, m.p. 198°–200° C. dec.: IR (CHCl$_3$): 2.84, 3.33, 5.95 (Sh), 5.97, 6.08, 6.17, 6.75, 6.88, 7.03 (br), 7.81, 8.18 (br), 8.53, 9.08, 9.41, 9.61 and 9.82 μ; NMR (CDCl$_3$): 7.53 (1, s, H—5), 6.79 (1, d, J = 8.5, H-2), 6.63 (1, d, J = 8.5 H—1), 6.34 (1, s, H—8), 5.10 (1, br. m., H—9), 3.90 (3, s, OCH$_3$—3), 3,75 (3, s, OCH$_3$—6)

and 3.17 (2, br. m. H—10); mass spectrum (high resolution 70 ev) molecular ion at m/e, 385.1516 (calculated for $C_{21}H_{23}O_6N$: 385.1525).

9R-N-ethoxycarbonyl-N-norsalutaridine can be prepared by substituting R-N-ethoxycarbonyl-N-norreticuline for the corresponding racemate in this Example.

EXAMPLE 3

(±)-N-Acetyl-N-norsalutaridine

The procedure of Example 1 was used, starting with 89.2 mg (0.25 mmol) of (±)-N-acetyl-N-norreticuline in place of (±)-N-trifluoroacetyl-N-norreticuline, to give 14.5 mg (16%) of the title compound, m.p. 137°–157° C. dec. (repeated recrystallization from chloroform/hexane did not improve the m.p.).

IR (CHCl₃): 2.85, 3.35, 5.99, 6.09, 6.14 (Sh), 6.75, 6.88, 6.99, 7.09. 7.57, 7.82, 8.14, 8.55, 9.11, 9.46, 9.80, 10.29, 10.76, 11.16 $\mu$; NMR (CDCl₃), 7.52 (1, s, H—5), 6.79 (1, d, J = 8.5, H—2), 6.63 (1, d, J = 8.5, H—1), 6.36 (1, s, H—8), 5.53 (1, t, J = 3.5, H—9), 3.89 (3, s, OCH₃—3), 3.74 (3, s, OCH₃—6), and 3.63 – 1.39 (complex m.); mass spectrum (high resolution 70 ev) molecular ion at m/e, 355.1419 (calculated for $C_{20}H_{21}O_5N$: 355.1419.

9R-N-Acetyl-N-norsalutaridine can be prepared by substituting R-N-acetyl-N-norreticuline for the corresponding racemate in this Example.

EXAMPLE 4

(±)-N-Cyclopropylcarbonyl-N-norsalutaridine

The procedure of Example 1 was used, starting with 96 mg (0.25 mmol) of (±)-N-cyclopropylcarbonyl-N-norreticuline in place of (±)-N-trifluoroacetyl-N-norreticuline, to give 10.2 mg (11%) of the title compound, m.p. 222°–226° C. dec.; IR (CHCl₃): 2.87. 3.38, 6.00, 6.12, 6.20, 6.39, 6.78, 7.04, 7.32, 7.60, 7.84, 8.14, 8.55, 8.90, 9.15 and 9.59 $\mu$; NMR (CDCl₃): 7.54, (1, s, H—5), 6.79 (1, d, J = 8.5, H—2), 6.63 (1, d, J = 8.5, H—1), 6.36 (1, s, H—8), 5.53 (1, br. s., H—9), 3.89 (3, s, OCH₃—6), 33.3–2.90 (4, br. m.); 2.78–2.42 (br. m.), 1.92–1.33 (br. m.), 1.24 (br. m.), and 1.09–0.56 (br. m.); mass spectrum (high resolution 70 ev) molecular ion at m/e, 381.1566 (calculated for $C_{22}H_{23}O_5N$: 381.1575).

9R-N-Cyclopropylcarbonyl-N-norsalutaridine can be prepared by substituting R-N-cyclopropylcarbonyl-N-norreticuline for the corresponding racemate in this Example.

EXAMPLE 5

(±)-N-Benzyloxycarbonyl-N-norsalularidine

The procedure of Example 1 was used, starting with 112 mg (0.25 mmol) of (±)-benzyloxycarbonyl-N-norreticuline in place of (±)-N-trifluoroacetyl-N-norreticuline, to give 23.7 mg (21%) of the title compound, m.p. 91°–96° C. dec.; IR (CHCl₃); 2.85, 3.34, 5.92 (Sh.), 5.99, 6.09, 6.19, 6.31, 6.77, 7.00 (Sh.), 7.11, 7.40, 7.60, 7.83, 8.16, 8.56, 9.12, 9.45, 9.68, 9.86, 10.27, 10.80, 11.15, 11.61, 12.11 $\mu$; NMR (CDCl₃): 7.52, (1, s, H—5), 7.39 and 7.32 (5, Ar. H) 6.76 (1, d, J = 8.5, H—2), 6.64 and 6.60 (1, d, J = 8.5, H—1), 6.37 and 6.31 (1, s, H—8), 5.21–5.04 (3, br. m), 3.90 (3, s, OCH₃—3), 3.74 (3, s, OCH₃—6), 3.22–3.01 (2, br. m., H—10), 2.91–2.73 (br. m.) and 2.63–2.48 (br. m.); mass spectrum (high resolution 70 ev) molecular ion at m/e, 447.1702 (calculated for $C_{26}H_{25}O_6N$: 447.1681).

9-N-Benzyloxycarbonyl-N-norsalutaridine can be prepared by substituting R-N-benzyloxycarbonyl-N-norreticuline for the corresponding racemate in this Example.

EXAMPLE 6

(±)-Norsalutaridine

A solution of 10 mg (0,024 mmol) of (±)-N-trifluoroacetylnorsalturidine, and 50 mg of potassium carbonate in 6 ml of methanol and 0.50 ml of water was stirred under nirogen atmosphere at room temperature for 10 hours. Solvent was removed at room temperature with the aid of nitrogen. Four ml of water was added to the oil residue and extracted with 3-20 ml portions of chloroform. The organic extracts were washed with water, dried over anhydrous sodium sulfate and evaporated under reduced pressure to give 7.0 mg of oil which crystallized from chloroform hexane to give 6.6 mg (0.021 mmol, 86%) of (±)-norsalutaridine, m.p. 175°–177°; IR (CHCl₃): 2.85, 5.99, 6.09, 6.18, 6.76, 6.87, 6.98, 7.82, 8.14 (br), and 9.41 $\mu$; NMR (CDCl₃): 7.55 (1, S, H—5), 6.76 (1, d, J = 8.5, H—2), 6.67 (1, d, J = 8.5, H—1), 6.28 (1S, H—8), 3.89 (3, S, OCH₃—3), 3.76 (3, S, OCH₃—6), 3.36 (1, dd, J = 17.5, 6.5, H$_a$—10) and 3.13 (1, d, 5 = 17.5, H$_b$—10).

9R-N-norsalutaridine can be prepared by substituting 9R-N-trifluoroacetylnorsalutaridine for the corresponding racemate in this Example.

EXAMPLE 7

(±)-Salutaridinol

To a solution of 5.0 mg (0.013 mmol) of (±)-N-ethoxycarbonylnorsalutaridine in 8.0 ml of freshly distilled tetrahydrofuran, 50 mg of lithium-aluminum hydride was added and refluxed for 10 hours. The reaction mixture was cooled, and slowly crystalline ammonium chloride and a few drops of water were added. The precipitants were removed by filtration and washed thoroughly with hot methanol (70 ml). The solvent from the combined filtrates was removed under reduced pressure, and the residue was dissolved in a few mls of chloroform.

The mixture was filtered and the chloroform was evaporated with the aid of nitrogen to give 3.7 mg (0.0112 mmol, 82%) of a 1:1 mixture of epimers of (±)-salutaridinol as an oil; IR(CHCl₃); 2.79 (Sh), 2.83, 3.41, 6.01, 6.20, 6.31, 6.76, 6.87, 6.98, 7.54, 7.83, 8.11, 8.66, 9.14, 9.54, 9.83, and 10.73 $\mu$; NMR (CDCl₃): 6.70, 6.69, (1, d, J = 8.3, H—2); 6.61, 6.60 (1, d, J = 8.3, H—1); 6.37, 6.34 (1, S, H—5); 5.82 (d, J = 4.0), 5.78 (d, J = 3.2) (total 1, H—8); 4.63 (d, J = 4.0), 4.56 (d, J = 3.2) (total 1, H—7); 3.85 (3, S, OCH₃—3), 3.68 (3, S, OCH₃—6), 3.51 (1, br. m.); 3.20 (1, dd, J = 4.5, 5.5); 2.94, 2.90 (1, dd, J = 4.5, 5.5); 2.57 (1, br. m.); and 2.43, 2.42 (3, S, —NCH₃).

Epimers of 9R-salutaridinol can be obtained by substituting 9R-N-ethoxycarbonylnorsalutaridine for the corresponding racemate in this Example.

EXAMPLE 8

(±)-Thebaine

A solution of 14 mg (0.0425 mmol) of oil of (±)-salutaridinol in 8 ml of 1N hydrochloric acid was stirred at room temperature for 1 hour. The solution was made basic with 10% sodium hydroxide and extracted with 3-15 ml. portions of chloroform. The extracts were washed with water, dried over anhydrous sodium sulfate, and evaporated under reduced pressure to afford 7.7 mg of crude oil residue which was purified by preparative tlc (silica gel, chloroform-acetone-methanol 5:4:1) to give 4.0 mg of pure oil residue which was crystallized from methanol/ether to give 3.3 mg (0.0106 mmol, 25%) of (±)-thebaine; m.p. 183°–186° (lit 184°–186°); IR (CHCl$_3$); 3.44, 6.21, 6.67, 6.96 (br), 7.31, 7.81, 8.00 (sh), 8.12, 8.75, 9.05 (br), 9.52, 9.75 (br. sh.), 9.82, 10.75 br. and 10.98 $\mu$; NMR (CDCl$_3$): 6.66 (1, d, j = 8.3, H-2), 6.59 (1, d, j = 8.3, H-1), 6.55 (1, d, j = 6.5, H—8), 5.29 (1, S, H—5), 5.04 (1, d, j = 6.5, H—7), 3.85 (3, S, OCH$_3$—3), 3.60 (3, S, OCH$_3$—6) and 2.46 (3, S, N—CH$_3$).

9R-Thebaine can be prepared by substituting 9R-salutardinol for the (±)-salutardinol in this Example.

EXAMPLE 9

(±)-Northebaine

To a solution of 5.0 mg (0.013 mmol) of (±)-nor-salutaridine in 3 ml of methanol, 50 mg of sodium borohydride was added at 0° C. and stirred for 2 hours. The solvent was removed under reduced pressure to yield an oily residue (~ 4.2 mg) of (±)-norsalutaridinol which without isolating was stirred with 5 ml of IN hydrochloric acid for 0.5 hour at room temperature. The solution was made basic with 10% sodium hydroxide and extracted with 3–15 ml portions of chloroform. The extracts were washed with water, dried over anhydrous sulfate, and evaporated under reduced pressure to give 4.2 mg of oil residue which displayed several spots on tlc (10% methanol/chloroform). Preparative tlc (silica gel 20 × 3, 10% methanol/chloroform) to give four bands, 1, 2, 3 and 4 in order of increasing polarity. Component 2 afforded 0.6 mg (0.002 mmol, 16%) of oil of (±)-northebaine; IR (CHCl$_3$): 3.42, 6.22, 6.67, 6.88, 7.00 (br), 7.28 (br), 7.82, and 8.12 $\mu$.

I claim:

1. Process for synthesizing an N-acyl-N-norsalutaridine of the formula:

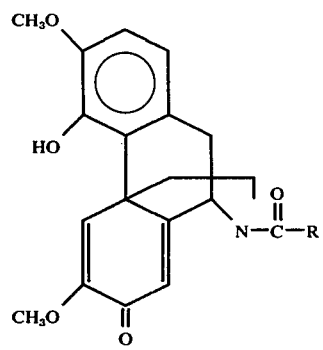

where R is hydrogen or an organic radical selected from
$C_1$–$C_{12}$ alkyl, $C_6$–$C_{12}$ aryl, $C_3$–$C_7$ cycloalkyl, $C_1$–$C_{12}$ alkoxy, $C_6$–$C_{12}$ aryloxy, $C_5$–$C_6$ cycloalkyloxy, $C_3$–$C_{12}$ alkenyloxy, halogen substituted $C_1$–$C_{12}$ alkyl, halogen substituted $C_6$–$C_{12}$ aryl, halogen substituted $C_3$–$C_7$ cycloalkyl, halogen substituted $C_1$–$C_{12}$ alkoxy, halogen substituted $C_6$–$C_{12}$ aryloxy, halogen substituted $C_5$–$C_6$ cycloalkoxy, halogen substituted $C_3$–$C_{12}$ alkenyloxy, $C_1$–$C_6$ alkyl substituted with $C_1$–$C_6$ alkoxy or $C_6$–$C_{12}$ aryl, $C_1$–$C_6$ alkoxy substituted with $C_1$–$C_6$ alkoxy or $C_6$–$C_{12}$ aryl, $C_6$–$C_{12}$ aryl substituted with 1-2 $C_1$–$C_2$ alkoxy radicals $C_6$–$C_{12}$ aryloxy substituted on the aryl portion of said aryl radical with 1-2 $C_1$–$C_2$ alkoxy radicals, $C_1$–$C_6$ alkyl substituted with $C_6$–$C_{12}$ aryl having 1-2 $C_1$–$C_2$ alkoxy radicals substituted on the aryl portion of said aryl radical and $C_1$–$C_6$ alkoxy substituted with $C_6$–$C_{12}$ aryl having 1-2 $C_1$–$C_2$ alkoxy radicals substituted on the aryl portion of said aryl radical, said halogen substituent being chlorine or fluorine and the number of substituents being from 1 to 7 which comprises reacting an N-acyl-N-norreticuline of the formula

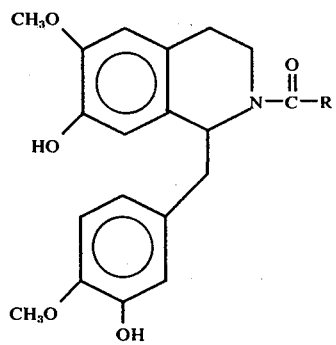

with thallium tristrifluoroacetate or with a coordinating agent selected from the trifluoroacetates, perchlorates, chlorides, bromides and iodides of palladium, copper, nickel, magnesium, calcium and lithium, and an oxidizing agent selected from manganese dioxide, silver carbonate, silver oxide, vanadyl chloride, ferric chloride and lead dioxide.

2. Process of claim 1 wherein R is selected from $C_1$–$C_3$ alkoxy, benzyloxy, methylbenzyloxy, trifluoromethyl, difluoromethyl, trichloromethyl, methyl, hydrogen and cyclopropyl.

3. Process of claim 1 wherein the N-acyl-N-norreticuline is contacted with thallium tristrifluoroacetate.

4. The process of claim 2 wherein the reaction is carried out under anhydrous conditions in a non-polar aprotic solvent; thallium tristrifluoroacetate is the coordinating and oxidizing agent; the reaction is at a temperature between about −95° C. and +25° C.; and the initial reaction temperature is maintained below the temperature at which oxidation occurs for a period of time to maximize formation of a coordination complex.

5. The process of claim 4 wherein the initial concentration of the N-acyl-N-norreticuline is about 0.0001 to 0.1 molar; the thallium tristrifluoroacetate is employed in an amount of 0.5 to 1.5 molar equivalent per mole of N-acyl-N-norreticuline; the solvent is dichloromethane, chloroform, benzene, trichloroethylene, tetrachloroethylene or carbon tetrachloride; and the initial reaction temperature is between −95° C. and −30° C.

6. The process of claim 5 wherein the reactants are held at a temperature between about −95° and −30° C. for an initial period of about one-half to three hours, and the temperature is then raised to between about −30° and +25° C. for about one-half to 10 hours.

7. The process of claim 4 wherein the N-acyl-N-norsalutaridine produced is converted to N-norsalutaridine.

8. The process of claim 4 wherein the N-acyl-N-norsalutaridine produced is converted to N-norsalutaridinol.

9. Process of claim 4 wherein R is ethoxy or benzyloxy.

10. Process of claim 1 wherein the starting material is an R-N-acyl-N-norreticuline and the product is a 9R-N-acyl-N-norsalutaridine.

11. Process of claim 4 wherein the starting material is an R-N-acyl-N-norreticuline and the product is a 9R-N-acyl-N-norsalutaridine.

12. Process of claim 9 wherein the starting material is an R-N-acyl-N-norreticuline and the product is a 9R-N-acyl-N-norsalutaridine.

13. An N-acyl-N-norsalutaridine of the formula

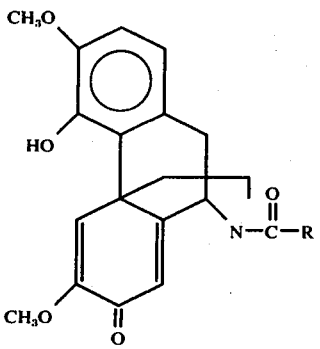

where R is hydrogen or an organic radical selected from
$C_1$–$C_{12}$ alkyl, $C_6$–$C_{12}$ aryl, $C_3$–$C_7$ cycloalkyl, $C_1$–$C_{12}$ alkoxy, $C_6$–$C_{12}$ aryloxy, $C_5$–$C_6$ cycloalkyloxy, $C_3$–$C_{12}$ alkenyloxy, halogen substituted $C_1$–$C_{12}$ alkyl, halogen substituted $C_6$–$C_{12}$ aryl, halogen substituted $C_3$–$C_7$ cycloalkyl, halogen substituted $C_1$–$C_{12}$ alkoxy, halogen substituted $C_6$–$C_{12}$ aryloxy, halogen substituted $C_5$–$C_6$ cycloalkoxy, halogen substituted $C_3$–$C_{12}$ alkenyloxy, $C_1$–$C_6$ alkyl substituted with $C_1$–$C_6$ alkoxy or $C_6$–$C_{12}$ aryl, $C_1$–$C_6$ alkoxy substituted with $C_1$–$C_6$ alkoxy or $C_6$–$C_{12}$ aryl, $C_6$–$C_{12}$ aryl substituted with 1–2 $C_1$–$C_{12}$ alkoxy radicals, $C_6$–$C_{12}$ aryloxy substituted on the aryl portion of said aryl radical with 1–2 $C_1$–$C_2$ alkoxy radicals, $C_1$–$C_6$ alkyl substituted with $C_6$–$C_{12}$ aryl having 1–2 $C_1$–$C_2$ alkoxy radicals substituted on the aryl portion of said aryl radical, and $C_1$–$C_6$ alkoxy substituted with $C_6$–$C_{12}$ aryl having 1–2 $C_1$–$C_2$ alkoxy radicals substituted on the aryl portion of said aryl radical, said halogen substituent being chlorine or fluorine and the number of substituents being from 1 to 7.

14. Compound of claim 13 where R is $C_1$–$C_3$ alkoxy, benzyloxy, methylbenzyloxy, trifluoromethyl, difluoromethyl, trichloromethyl, methyl, hydrogen, or cyclopropyl.

15. Compound of claim 13 wherein R is ethoxy or benzyloxy.

16. 9R-Enantiomer of a compound of claim 13.

17. 9R-Enantiomer of a compound of claim 14.

18. 9R-Enantiomer of a compound of claim 15.

19. 9R-N-norsalutaridine.

* * * * *

UNITED STATES PATENT AND TRADEMARK OFFICE
CERTIFICATE OF CORRECTION

PATENT NO. : 4,003,903
DATED : January 18, 1977
INVENTOR(S) : Martin Alan Schwartz It is certified that error appears in the above-identified patent and that said Letters Patent are hereby corrected as shown below:

Col. 2, Formula 2, bond between 12 and 13 ---
Col. 1, formula 3, bond between 12 and 13 ---
Col. 6, lines 14,15 and 16, "R" should read  $\underline{R}$ ---
Col. 8, lines 27,35 and 45, "N" should read  $\underline{N}$ ---
Col. 9, line 17, "16" should read  $\underline{16}$ ---
Col. 10, line 21 and 49, "Anal." should read  $\underline{Anal.}$ ---
Col. 10, line 52, "R" should read  $\underline{R}$ ---
Col. 11, line 4, "R" should read  $\underline{R}$ ---
Col. 11, lines 27 and 28, "R" should read  $\underline{R}$ ---
Col. 11, line 42, "(-6)" should read   (-3)  and  3.74(3,s,OCH$_3$-6)
          was left out ---
Col. 11, line 42, "33.3" should read  3.33 ---
Col. 11, line 43, "(br.m)" second occurrence should read --(br.s)--.
Col. 11, lines 47 and 48, "R" should read  $\underline{R}$ ---
Col. 12, lines 3 and 4, "R" should read  $\underline{R}$ ---
Col. 12, line 12, "fluoroacetylnorsalturidine" should read
          fluoroacetylnorsa$\underline{l}$utaridine ---
Col. 12, line 14, "nirogen" should read  nitrogen ---
Col. 12, lines 29 and 30, "R" should read  $\underline{R}$ ---
Col. 12, lines 59 and 60, "R" should read  $\underline{R}$ ---
Col. 13, lines 17 and 18, "R" should read  $\underline{R}$ ---
Col. 2, line 13, "Reticulene" should read  Reticuline ---

UNITED STATES PATENT AND TRADEMARK OFFICE
CERTIFICATE OF CORRECTION

PATENT NO. : 4,003,903

DATED : January 18, 1977

INVENTOR(S) : Martin Alan Schwartz

It is certified that error appears in the above-identified patent and that said Letters Patent are hereby corrected as shown below:

In the Claims

Col. 13, line 68, "c" should read C ---

Col. 16, line 13, "$C_1-C_{12}$" should read $C_1-C_2$ ---

Signed and Sealed this

Twenty-sixth Day of April 1977

[SEAL]

Attest:

RUTH C. MASON
Attesting Officer

C. MARSHALL DANN
Commissioner of Patents and Trademarks